(12) United States Patent
Bhasale et al.

(10) Patent No.: US 8,901,128 B2
(45) Date of Patent: Dec. 2, 2014

(54) PHARMACEUTICAL COMPOSITIONS OF RANOLAZINE

(75) Inventors: Ketan Bhasale, Pune (IN); Raghavendra Naik, Pune (IN); Subhasis Das, Pune (IN); Vijaya Kumar Thommandru, Pune (IN)

(73) Assignee: Lupin Limited, Mumbai, Maharashtra (IN)

( * ) Notice: Subject to any disclaimer, the term of this patent is extended or adjusted under 35 U.S.C. 154(b) by 0 days.

(21) Appl. No.: 13/322,846

(22) PCT Filed: May 26, 2010

(86) PCT No.: PCT/IN2010/000356
§ 371 (c)(1),
(2), (4) Date: Nov. 28, 2011

(87) PCT Pub. No.: WO2010/137040
PCT Pub. Date: Dec. 2, 2010

(65) Prior Publication Data
US 2012/0077817 A1 Mar. 29, 2012

(30) Foreign Application Priority Data
May 28, 2009 (IN) .............................. 801/KOL/2009

(51) Int. Cl.
*A61K 31/495* (2006.01)
*A61K 9/22* (2006.01)
*A61K 9/20* (2006.01)

(52) U.S. Cl.
CPC ............. *A61K 9/2013* (2013.01); *A61K 31/495* (2013.01); *A61K 9/2077* (2013.01)
USPC ...... 514/252.12; 424/457; 424/468; 424/489; 424/498

(58) Field of Classification Search
CPC . A61K 9/2013; A61K 31/496; A61K 31/495; A61K 9/2077

USPC ............. 514/252.12; 424/400, 451, 457, 464, 424/468, 489, 498
See application file for complete search history.

(56) References Cited

U.S. PATENT DOCUMENTS

| | | | |
|---|---|---|---|
| 4,567,264 A | 1/1986 | Kluge | |
| 5,472,707 A | 12/1995 | Samuels | |
| 5,506,229 A | 4/1996 | Dow | |
| 6,303,607 B1 | 10/2001 | Wolff | |
| 6,503,911 B2 * | 1/2003 | Wolff et al. | .............. 514/252.13 |
| 2006/0177502 A1 | 8/2006 | Sastry | |

FOREIGN PATENT DOCUMENTS

CN 1891218 A * 1/2007 ................ A61P 9/00

OTHER PUBLICATIONS

Rodriguez-Spong et al. Advanced Drug Delivery Reviews 2004, 56, 241-274.*
Longer et al. Sustained Release Drug Discovery Systems. In Pharmaceutical Sciences; Mack Publishing Company: Easton, PA, 1990; pp. 1676-1693.*
Udho Thadini et al., Double-Blind Efficacy and Safety Study of a Novel Anti-Ischemic Agent, Ranolazine, Versus Placebo in Patients With Chronic Stable Angina Pectoris, Circulation, American Heart Association, 90:726-734 (1994).

* cited by examiner

*Primary Examiner* — Sreeni Padmanabhan
*Assistant Examiner* — Irina Neagu
(74) *Attorney, Agent, or Firm* — Novak Druce Connolly Bove + Quigg LLP

(57) ABSTRACT

A novel controlled release pharmaceutical dosage form comprising a therapeutically effective amount of ranolazine or pharmaceutically acceptable salt(s), polymorph(s), solvate(s), hydrate(s), enantiomer(s) thereof, one or more lipid(s) as release controlling agent(s) and one or more pharmaceutically acceptable excipient(s).

6 Claims, No Drawings

PHARMACEUTICAL COMPOSITIONS OF RANOLAZINE

FIELD OF THE INVENTION

The present invention relates to a novel controlled release pharmaceutical dosage form comprising a therapeutically effective amount of ranolazine or pharmaceutically acceptable salt(s), polymorph(s), solvate(s), hydrate(s), enantiomer(s) thereof, one or more lipid(s) as release controlling agent(s) and one or more pharmaceutically acceptable excipient(s).

BACKGROUND OF THE INVENTION

Ranolazine was first described in U.S. Pat. No. 4,567,264, the specification of which discloses ranolazine, (±)-N-(2,6-dimethylphenyl)-4-[2-hydroxy-3-(2-methoxyphenoxy)-propyl]-1- piperazineacetamide, and its pharmaceutically acceptable salts, and their use in the treatment of cardiovascular diseases, including arrhythmias, variant and exercise induced angina, and myocardial infarction.

U.S. Pat. No. 5,506,229 discloses the use of ranolazine and its pharmaceutically acceptable salts and esters for the treatment of tissues experiencing a physical or chemical insult, including cardioplegia, hypoxic or reperfusion injury to cardiac or skeletal muscle or brain tissue, and for use in transplants. Conventional oral and parenteral formulations are disclosed, including controlled release formulations. In particular, Example 7D of U.S. Pat. No. 5,506,229 describes a controlled release formulation in capsule form comprising microspheres of ranolazine and microcrystalline cellulose coated with release controlling polymers.

U.S. Pat. No. 5,472,707 discloses a high-dose oral formulation employing supercooled liquid ranolazine as a fill solution for a hard or soft gelatin capsule.

A study published in Circulation 90:726-734 (1994) demonstrated that ranolazine was ineffective as an antianginal and anti-ischemic agent when administered as an IR formulation. As set forth in literature, the initial trials of ranolazine on humans suffering from angina were failures. The trials used an immediate release of ranolazine formulation at a dose level of 120 mg taken three times daily. Based upon the initial experiments, it was uncertain whether or not ranolazine could be given to humans in an amount and mode that is effective against angina.

One problem with conventional oral dosage formulations is that they are not ideally suited to ranolazine and its pharmaceutically acceptable salts, because the solubility of ranolazine is relatively high at the low pH that occurs in the stomach. Furthermore ranolazine also has a relatively short plasma half-life. The high acid solubility property of ranolazine results in rapid drug absorption and clearance, causing large and undesirable fluctuations in plasma concentration of ranolazine and a short duration of action, thus necessitating frequent oral administration for adequate treatment.

There was therefore a need for a method for administering ranolazine in an oral dosage form once or twice daily that provides therapeutically effective plasma concentrations of ranolazine for the treatment of angina in humans.

Currently Ranolazine is marketed as modified release tablets at the dosage of 500 mg and 1 gm under the brand name Ranexa®.

U.S. Pat. No. 6,303,607 discloses a sustained release pharmaceutical dosage form including at least 50% by weight ranolazine and an admixture of at least one pH-dependent binder and at least one pH-independent binder, and wherein the peak to trough plasma ranolazine level does not exceed 3:1 over a 24 hour period.

U.S. Pat. Application No. 20060177502A1 discloses a sustained release pharmaceutical formulation comprising: less than 50% ranolazine, a pH dependent binder; a pH independent binder and one or more pharmaceutically acceptable excipients.

However, there still exists a need to prepare novel controlled release dosage forms of Ranolazine or pharmaceutically acceptable salt(s), polymorph(s), solvate(s), hydrate(s), enantiomer(s) thereof which are simple to manufacture yet robust that provides therapeutically effective plasma concentrations of ranolazine for the treatment of angina in humans.

OBJECTS OF THE INVENTION

A novel controlled release pharmaceutical dosage form comprising a therapeutically effective amount of ranolazine or pharmaceutically acceptable salt(s), polymorph(s), solvate(s), hydrate(s), enantiomer(s) thereof, one or more lipid(s) as release controlling agent(s) and one or more pharmaceutically acceptable excipient(s).

A novel controlled release pharmaceutical dosage form comprising a therapeutically effective amount of ranolazine or pharmaceutically acceptable salt(s), polymorph(s), solvate(s), hydrate(s), enantiomer(s), one or more lipid(s) as release controlling agent(s) and one or more pharmaceutically acceptable excipient(s) wherein ranolazine is at least about 20% w/w of the total formulation.

A process for preparing novel controlled release dosage form ranolazine or pharmaceutically acceptable salt(s) or enantiomer(s) or polymorph(s) thereof, wherein the process comprises the steps of blending ranolazine with one or more pharmaceutically acceptable excipient(s), melting the lipid component and dispersing the blend of ranolazine with the lipid component, cooling the blend, mixing with other excipient(s) and then compressing the granules to form the solid oral dosage form.

A novel controlled release pharmaceutical dosage form comprising a therapeutically effective amount of ranolazine or pharmaceutically acceptable salt(s), polymorph(s), solvate(s), hydrate(s), enantiomer(s), one or more lipid(s) as release controlling agent(s) and one or more pharmaceutically acceptable excipient(s) wherein about 0% to about 40% of said ranolazine is released after 2 hours; from about 40% to about 80% of said ranolazine is released after 8 hours; not less than about 75% of said ranolazine is released after 24 hours.

DETAILED DESCRIPTION OF THE INVENTION

The present invention relates to a novel controlled release pharmaceutical dosage form comprising a therapeutically effective amount of ranolazine or pharmaceutically acceptable salt(s), polymorph(s), solvate(s), hydrate(s), enantiomer(s) thereof, one or more lipid(s) as release controlling agent(s) and one or more pharmaceutically acceptable excipient(s).

As used herein, "pharmaceutically acceptable salts" refer to derivatives of the ranolazine wherein ranolazine is modified by reacting it with an acid or base as needed to form an ionically bound pair. Examples of pharmaceutically acceptable salts include conventional non-toxic salts or the quaternary ammonium salt of the parent compound formed, for example, from non-toxic inorganic or organic acids. Suitable non-toxic salts include those derived from inorganic acids such as hydrochloric, hydrobromic, sulfuric, sulfamic, phosphoric, nitric, and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenyl acetic, benzoic, salicylic, sulfanilic, fumaric, oxalic, isethionic, and others known to those of ordinarily skilled in the art.

Ranolazine is present in at least about 20% w/w of the total formulation.

The term "controlled release" as used herein in relation to the dosage form means which is not immediate release and is taken to encompass controlled release, sustained release, prolonged release, timed release, retarded release, extended release and delayed release. Controlled release can be used interchangeably with prolonged release, programmed release, timed release, extended release, sustained release and other such dosage forms.

By "pharmaceutically acceptable" is meant excipient(s) comprised of a material that is not biologically or otherwise undesirable.

The release controlling polymers comprise of lipid such as fat(s), oil(s), wax(s) or combinations thereof.

Fats are generally triesters of glycerol and fatty acids. Suitable fats and fatty substances include but not limited to fatty alcohols (such as lauryl, myristyl, stearyl, cetyl or cetostearyl alcohol), fatty acids and derivatives, including but not limited to fatty acid esters, fatty acid glycerides (mono-, di- and tri-glycerides), and hydrogenated fats. Fats may be either solid or liquid at normal room temperature, depending on their structure and composition. Although the words "oils", "fats", and "lipids" are all used to refer to fats, "oils" is usually used to refer to fats that are liquids at normal room temperature, while "fats" is usually used to refer to fats that are solids at normal room temperature. "Lipids" is used to refer to both liquid and solid fats, along with other related substances The fats include but not limited to oil, which is an animal (e.g., fatty acid esters), mineral (e.g., paraffin oils), vegetable (e.g., vegetable oils), or synthethic hydrocarbons that are liquid at room temperature, soluble in organic solvents, and substantially not soluble in water. Examples of oils include but are not limited to: mineral oils such as paraffin oils; synthetic hydrocarbons such as polybutene and polyisobutene; vegetable oils such as castor oils, hydrogenated vegetable oil, sesame oils, and peanut oils; and animal oils and fats such as triglycerides and butters. Partially hydrogenated vegetable oils are derived from natural products and generally comprise a mixture of glycerides of $C_{14-20}$ fatty acids, in particular palmitic and stearic acids. Suitable examples of partially hydrogenated vegetable oils include partially hydrogenated cottonseed oil, soybean oil, corn oil, peanut oil, palm oil, sunflower seed oil or mixtures thereof. Chemical equivalents of partially hydrogenated vegetable oils include synthetically produced glycerides of $C_{14-20}$ fatty acids having the same properties as the naturally derived products as hereinbefore described.

Waxes are similar to oils, except that unlike oils, waxes are not liquid at room temperature. Waxes include but not limited to animal waxes, plant waxes, mineral waxes, and petroleum waxes. Examples of waxes include, but are not limited to, glyceryl behenate, glyceryl monosterate, stearic acid, palmitic acid, lauric acid, carnauba wax, cetyl alcohol, glyceryl stearate beeswax, paraffin wax, ozokerite, candelilla wax, cetyl alcohol, stearyl alcohol, spermaceti, carnauba wax, baysberry wax, montan, ceresin, and microcrystalline waxes.

Pharmaceutically acceptable excipient(s) include but are not limited to diluents, lubricants, disintegrants, glidants and surface-active agents.

The amount of excipient employed will depend upon how much active agent is to be used. One excipient can perform more than one function.

Fillers or diluents, which include, but are not limited to confectioner's sugar, compressible sugar, dextrates, dextrin, dextrose, fructose, lactitol, mannitol, sucrose, starch, lactose, xylitol, sorbitol, talc, microcrystalline cellulose, calcium carbonate, calcium phosphate dibasic or tribasic, calcium sulphate, and the like can be used.

Lubricants may be selected from, but are not limited to, those conventionally known in the art such as Mg, Al or Ca or Zn stearate, polyethylene glycol, glyceryl behenate, mineral oil, sodium stearyl fumarate, stearic acid, hydrogenated vegetable oil and talc.

Glidants include, but are not limited to, silicon dioxide; magnesium trisilicate, powdered cellulose, starch, talc and tribasic calcium phosphate, calcium silicate, magnesium silicate, colloidal silicon dioxide, silicon hydrogel and other materials known to one of ordinary skill in the art.

The present dosage forms may optionally contain disintegrants which include but are not limited to starches; clays; celluloses; alginates; gums; cross-linked polymers, e.g., cross-linked polyvinyl pyrrolidone or crospovidone, e.g., POLYPLASDONE XL, cross-linked sodium carboxymethylcellulose or croscarmellose sodium, e.g., AC-DI-SOL from FMC; and cross-linked calcium carboxymethylcellulose; and guar gum. Use of disintegrant according to the present invention facilitates in the release of drug in the latter stage and thereby completely releasing the drug from the dosage form.

The present dosage forms may optionally contain a surface-active agent. The preferred agent is copolymers composed of a central hydrophobic chain of polyoxypropylene (poly (propylene oxide)) and polyoxyethylene (poly (ethylene oxide)) that is well known as poloxamer. However, other agents may also be employed such as dioctyl sodium sulfosuccinate (DSS), triethanolamine, sodium lauryl sulphate (SLS), polyoxyethylene sorbitan and poloxalkol derivatives, quaternary ammonium salts or other pharmaceutically acceptable surface-active agents known to one ordinary skilled in the art.

The dosage form according to the present invention include but is not limited to tablets, pellets, beads, granules, capsules, microcapsules and tablets in capsules.

The pharmaceutical dosage forms of the invention may further be film coated.

The preferred film coating of this invention is comprised of a commercial film-coating product designed for aqueous film coating containing the water-soluble, film-forming resin, such a product is commercially available under the trade name Opadry White™ (Colorcon, West Point, Pa.).

These coating comprises one or more excipients selected from the group comprising coating agents, opacifiers, fillers, plasticizers, polishing agents, colouring agents, antitacking agents and the like.

The pharmaceutical dosage form of the invention can be formed by various methods known in the art such as by dry granulation, wet granulation, melt granulation, direct compression, double compression, extrusion spheronization, layering and the like.

Novel controlled release matrix tablet according to the present invention are manufactured preferably as per the following procedure:
i) blend ranolazine and one or more pharmaceutically acceptable excipients,
ii) melt hydrogenated vegetable oil
iii) disperse step (i) with step (ii) under continuous and uniform stirring conditions iv) cool step (iii), pass it through suitable sieve, further mix it with other excipient(s)
v) compressing step (iv) to form the solid oral dosage form.
vi) the dosage form is further coated.

The examples given below are illustrative embodiments of the invention and are merely exemplary. A person skilled in the art may make variations and modifications without deviating from the spirit and scope of the invention. All such modifications and variations are intended to be included within the scope of the invention.

EXAMPLES

Example 1

| S. No. | Ingredients | % w/w |
| --- | --- | --- |
| 1 | Ranolazine | 62.5 |
| 2 | Hydrogenated vegetable oil | 25.0 |
| 3 | Lactose | 11.0 |
| 4 | Colloidal silicon dioxide | 0.5 |
| 5 | Magnesium stearate | 1.0 |

Brief manufacturing procedure:

Hydrogenated vegetable oil was melted and Ranolazine was uniformly dispersed under continuous and uniform stirring conditions and allowed to solidify. The material was passed through a suitable sieve to form granules. The granules were blended with lactose, colloidal silicon dioxide. This blend was lubricated with magnesium stearate and compressed into tablets.

Example 2

| S. No. | Ingredients | % w/w |
| --- | --- | --- |
| 1 | Ranolazine | 55.0 |
| 2 | Glyceryl behenate | 30.0 |
| 3 | Lactose | 13.5 |
| 4 | Colloidal silicon dioxide | 0.5 |
| 5 | Magnesium stearate | 1.0 |

Brief manufacturing procedure:

Glyceryl behenate was melted and Ranolazine was uniformly dispersed under continuous and uniform stirring conditions and allowed to solidify. The material was passed through a suitable sieve to form granules. The granules were blended with lactose, colloidal silicon dioxide. This blend was lubricated with magnesium stearate and compressed into tablets.

Example 3

| S. No. | Ingredients | % w/w |
| --- | --- | --- |
| 1 | Ranolazine | 60.0 |
| 2 | Glyceryl Monostearate | 30.0 |
| 3 | Lactose | 8.5 |
| 4 | Colloidal silicon dioxide | 0.5 |
| 5 | Magnesium stearate | 1.0 |

Brief manufacturing procedure:

Glyceryl Monostearate was melted and Ranolazine was uniformly dispersed under continuous and uniform stirring conditions and allowed to solidify. The material was passed through a suitable sieve to form granules. The granules were blended with lactose, colloidal silicon dioxide. This blend was lubricated with magnesium stearate and compressed into tablets.

Example 4

| S. No. | Ingredients | % w/w |
| --- | --- | --- |
| 1 | Ranolazine | 30.0 |
| 2 | Hydrogenated vegetable oil | 35.0 |
| 3 | Lactose | 33.5 |
| 4 | Colloidal silicon dioxide | 0.5 |
| 5 | Magnesium stearate | 1.0 |

Brief manufacturing procedure:

Hydrogenated vegetable oil was melted and Ranolazine was uniformly dispersed under continuous and uniform stirring conditions and allowed to solidify. The material was passed through a suitable sieve to form granules. The granules were blended with lactose, colloidal silicon dioxide. This blend was lubricated with magnesium stearate and compressed into tablets.

In-vitro dissolution details

The formulations of the invention have a prolonged in vitro release rate. The in vitro test used to measure release rate of the active agent from a formulation of the invention was as follows. A solution of 900 ml of a 0.1 N HCl was placed in an apparatus capable of agitation. The apparatus contained a paddle and rotated at a speed of 50 rpm. The tablet formulation was placed in the apparatus and dissolution was periodically measured. The in vitro dissolution studies of Example 1 is as follows

| Time (Hr) | % Drug Release |
| --- | --- |
| 2 | about 20-about 30 |
| 4 | about 30-about 40 |
| 8 | about 40-about 60 |
| 12 | about 55-about 70 |
| 16 | about 70-about 80 |
| 20 | about 75-about 85 |
| 24 | about 80-about 90 |

The invention claimed is:

1. A novel controlled release pharmaceutical dosage form comprising:
   a therapeutically effective amount of Ranolazine free base;
   at least one lipid as release controlling modifying agent; and
   at least one pharmaceutically acceptable excipient wherein about 80% to about 90% of Ranolazine is released at 24 hours.

2. The novel controlled release pharmaceutical dosage form according to claim 1, wherein the at least one lipid is selected from the group consisting of a fat, an oil, and a wax.

3. The novel controlled release pharmaceutical dosage form according to claim 1, wherein pharmaceutically acceptable excipients are selected from the group comprising diluents, lubricants, surfactants, and glidants.

4. The novel controlled release pharmaceutical dosage form according to claim 1, wherein the dosage form includes one selected from the group consisting of tablets, capsules, pellets, granules, and mixtures thereof.

5. The novel controlled release pharmaceutical dosage form according to claim 1: wherein Ranolazine is at least-more than about 30% w/w of the total formulation.

6. A process for preparing novel controlled release dosage form of Ranolazine free base, wherein the process comprises:
- blending Ranolazine with at least one pharmaceutically acceptable excipient comprising a lipid component to form a blend;
- melting the lipid component;
- dispersing the blend of Ranolazine with the lipid component;
- cooling the blend to form granules;
- sifting the granules:
- mixing the granules with an excipient, and
- compressing the granules to form a solid oral dosage the tablet wherein about 80% to about 90% of Ranolazine is released at 24 hours from the said dosage form.

* * * * *